(12) United States Patent
Hsieh et al.

(10) Patent No.: US 9,360,436 B2
(45) Date of Patent: Jun. 7, 2016

(54) INSPECTION DEVICE AND INSPECTION METHOD (71) Applicant: Industrial Technology Research Institute, Hsinchu (TW)

(72) Inventors: Yi-Chen Hsieh, Changhua County (TW); Chih-Jung Chiang, Hsinchu County (TW); Fu-Cheng Yang, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 316 days.

(21) Appl. No.: 14/079,568

(22) Filed: Nov. 13, 2013

(65) Prior Publication Data

US 2014/0168417 A1 Jun. 19, 2014

(30) Foreign Application Priority Data

Dec. 18, 2012 (TW) .............................. 101147993 A (51) Int. Cl.
 *G01N 21/88* (2006.01)
 *G01N 21/21* (2006.01)
 *G02B 5/30* (2006.01)
 *G01N 21/95* (2006.01)

(52) U.S. Cl.
 CPC ............ *G01N 21/8806* (2013.01); *G01N 21/21* (2013.01); *G01N 21/9501* (2013.01); *G01N 2021/8848* (2013.01); *G02B 5/3066* (2013.01)

(58) Field of Classification Search
 CPC ... G02B 5/3066; G01N 21/8806; G01N 21/21
 See application file for complete search history.

(56) References Cited

U.S. PATENT DOCUMENTS

| | | | |
|---|---|---|---|
| 4,591,723 A | 5/1986 | Akiyama |
| 5,198,913 A | 3/1993 | Toyoda et al. |
| 5,247,344 A | 9/1993 | Doan |
| 5,333,052 A | 7/1994 | Finarov |
| 5,450,201 A | 9/1995 | Katzir et al. |
| 5,844,682 A | 12/1998 | Kiyomoto et al. |
| 6,134,013 A | 10/2000 | Sirat et al. |
| 6,175,645 B1 | 1/2001 | Elyasaf et al. |
| 6,215,549 B1 | 4/2001 | Suzuki et al. |

(Continued)

FOREIGN PATENT DOCUMENTS

| | | |
|---|---|---|
| CN | 1959395 A | 5/2007 |
| JP | 2006105884 | 4/2006 |

(Continued)

OTHER PUBLICATIONS

China Patent Office, Office Action, Patent Application Serial No. 201210581334.3, Nov. 3, 2015, China.

(Continued)

*Primary Examiner* — Joseph Ustaris
*Assistant Examiner* — Zhubing Ren (57) ABSTRACT The disclosure provides an inspection device including a light source module, an image receiving module and a processing unit. The light source module emits a first incident light and a second incident light to a device under test (DUT). The image receiving module receives a first image corresponding to the DUT irradiated by the first incident light, and receives a second image corresponding to the DUT irradiated by the second incident light. The processing unit calculates the contrast ratio of the first image and the second image to obtain a high-contrast image for inspection.

18 Claims, 6 Drawing Sheets

(56) References Cited

U.S. PATENT DOCUMENTS

| | | | |
|---|---|---|---|
| 6,304,326 B1 | 10/2001 | Aspnes et al. | |
| 6,813,026 B2 | 11/2004 | McAninch | |
| 7,094,609 B2 | 8/2006 | Demers | |
| 7,145,654 B2 | 12/2006 | Norton | |
| 7,397,552 B2 | 7/2008 | Guetta et al. | |
| 7,580,133 B2 | 8/2009 | Ueki et al. | |
| 7,826,047 B2 | 11/2010 | Shibata et al. | |
| 8,253,536 B2 | 8/2012 | Kaminska et al. | |
| 2003/0021462 A1* | 1/2003 | Sakai | G06T 7/001 382/144 |
| 2007/0047801 A1 | 3/2007 | Kojima et al. | |
| 2007/0253033 A1 | 11/2007 | Johansen et al. | |
| 2010/0014083 A1* | 1/2010 | Ueno | G01N 21/9501 356/364 |
| 2010/0245810 A1 | 9/2010 | Hayashi et al. | |

FOREIGN PATENT DOCUMENTS

| | | |
|---|---|---|
| JP | 2007-57521 A | 3/2007 |
| TW | 200844427 | 11/2008 |
| TW | 200912287 | 3/2009 |
| TW | 201017150 | 5/2010 |
| TW | M380471 | 5/2010 |
| TW | 201105957 | 2/2011 |
| WO | WO 2008/087960 | 7/2008 |

OTHER PUBLICATIONS

China Patent Office, Notice of Allowance, Patent Application Serial No. 201210581334.3, Feb. 3, 2016, China.

Taiwan Patent Office, Office Action, Patent Application Serial No. 101147993, Aug. 7, 2014, Taiwan.

Chien-Yuan Han et al., "Photoelastic Modulated Imaging Ellipsometry by Stroboscopic Illumination Technique," Review of Scientific Instruments, Feb. 2006, 6 pages, AIP, US.

Yu Faye Chao et al., "Index Profile of Radial Gradient Index Lens Measured by Imaging Ellipsometric Technique," Japanese Journal of Applied Physics, Feb. 2005, pp. 1111-1114, vol. 44, No. 2, The Japan Society of Applied Physics, US.

"Introduction to the Technology of Polarizing Image Inspection," Nov. 2007, 10 pages. ITRI, Taiwan.

"Research on Multi-Length Ellipsometry Image Contrasts of Film Etching Patterns," Oct. 2007, 6 pages, ITRI, Taiwan.

Hau-Wei Wang et al., "Whole Visible Range Imaging Ellipsometry," Proc. of SPIE, Nov. 2007, pp. 67230Q-1-67230Q-6, SPIE, US.

* cited by examiner

INSPECTION DEVICE AND INSPECTION METHOD

CROSS REFERENCE TO RELATED APPLICATIONS

This application claims priority of Taiwan Patent Application No. 101147993, filed on Dec. 18, 2012, the entirety of which is incorporated by reference herein.

BACKGROUND

1. Field of the Disclosure

The present disclosure relates to a film inspection method, and in particular, relates to a method of inspecting defects of a film by enhancing the image contrast.

2. Description of the Related Art

Traditionally, the method of PCSA (Polarizer Compensator Sample Analyzer) enhancing contrast for image inspection is to find the configuration of the null image (i.e., full-dark image), so that the defect region and the non-defect region display a bright gray-scale image and a dark gray-scale image. A full-dark image is arranged to enhance the image contrast of another region. The angles of the analyzer and the polarizer are rotated during operation, and the gray-scale value of one of the regions gradually decreases to the full-dark value. Generally, in order to attain a full-dark configuration, the polarizer and the analyzer are adjusted by turn and the variation of the gray-scale value of a camera? is constantly inspected. Therefore, the optimum angle of the polarizer and analyzer can be obtained with the full-dark image. It takes time to find the full-dark image by switching between polarization states to determine the gray-scale value of the camera. In addition, the light intensity and rotation angle of the elements are calculated based upon trigonometric functions. Also, the sensitivity is lower when the intensity is low. Therefore, it is more difficult to determine the gray-scale value, and it takes more time for the system to find the full-dark image and the optimum image contrast.

Therefore, a new method is needed to solve the above problems.

SUMMARY

The inspection device and the inspection method according to the present disclosure utilizes two incident lights with two different polarizing configurations to generate two sets of different images in order to enhance the image. Furthermore, the inspection device and the inspection method according to the present disclosure reduce the correction of the polarizing elements and enhances the contrast of the optimal image to decrease process time.

The present disclosure provides an inspection device comprising a light source module, an image receiving module and a processor. The light source module emits a first incident light and a second incident light to a device under test (DUT). The image receiving module receives a first image generated by the DUT irradiated by the first incident light and a second image generated by the DUT irradiated by the second incident light. The processor calculates a contrast value of the first image and the second image to obtain a high contrast image for inspection.

The present disclosure provides an inspection method applied to an inspection device, wherein the inspection device comprises a light source module, an image receiving module and a processor. The inspection method comprises: emitting a first incident light and a second incident light to a device under test by the light source module; receiving a first image generated by the DUT irradiated by the first incident light and a second image generated by the DUT irradiated by the second incident light; and calculating a contrast value of the first image and the second image to obtain a high contrast image for inspection by the processor.

A detailed description is given in the following embodiments with reference to the accompanying drawings.

BRIEF DESCRIPTION OF DRAWINGS

The present disclosure can be more fully understood by reading the subsequent detailed description and examples with references made to the accompanying drawings, wherein.

DETAILED DESCRIPTION

The following description is of the best-contemplated mode of carrying out the disclosure. This description is made for the purpose of illustrating the general principles of the disclosure and should not be taken in a limiting sense. The scope of the disclosure is best determined by reference to the appended claims.

Figure 1:
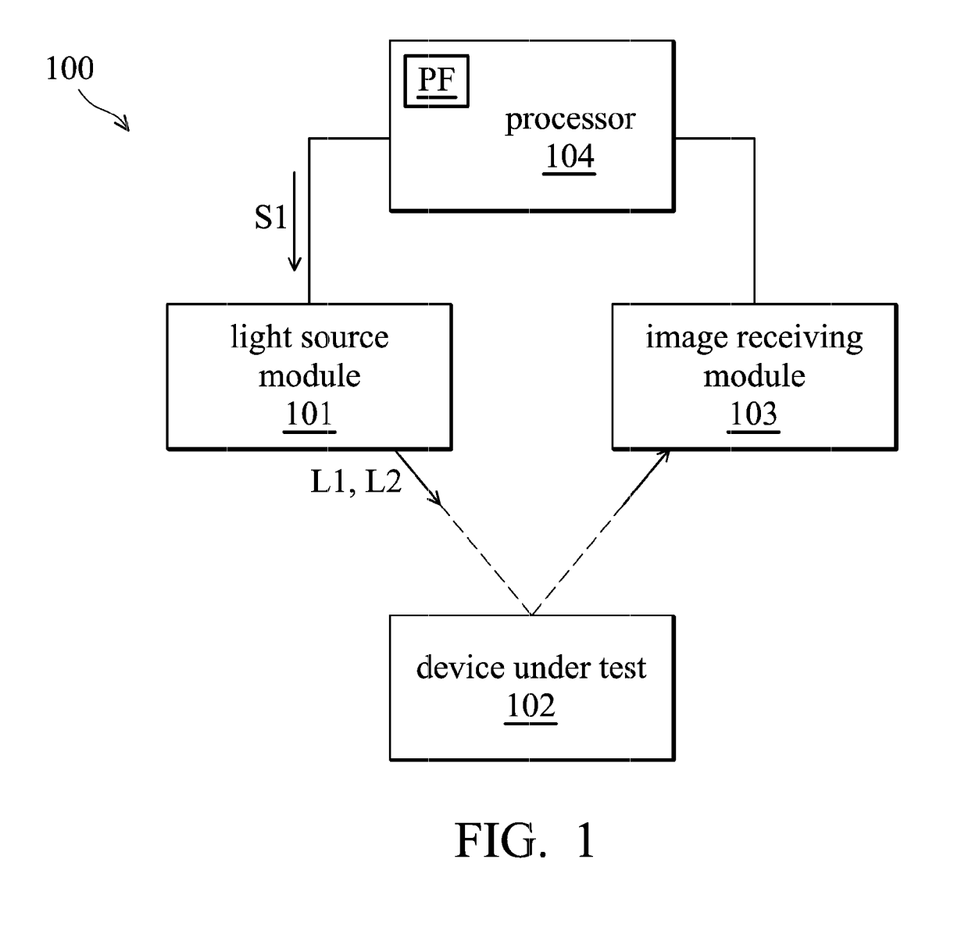
FIG. 1 is a schematic diagram of an inspection device according to the present disclosure.

FIG. 1 is the schematic diagram of an inspection device according to the present disclosure. As shown in FIG. 1, the inspection device 100 includes a light source module 101, a device under test (DUT) 102, an image receiving module 103 and a processor 104. The inspection device 100 can be applied for the measurement of optical characteristics, semiconductor characteristics and micro-electronic characteristics. For example, the inspection device 100 is arranged to detect the physical parameters of a device under test 102, such as the thickness, the refractive index and the gray-scale value of an image of the device under test 102. The device under test 102 can be a film material, a semiconductor material, an optical material, an organic material or a non-organic material which is arranged on a wafer or a substrate. In an embodiment, the device under test 102 includes two kinds of film materials on the substrate comprising an amorphous silicon material and a poly-silicon material, and is not limited thereto.

The light source 101 is arranged to emit a first incident light L1 and a second incident light L2 to the device under test 102. The device under test 102 reflects the first incident light L1 and the second incident light L2 to the image receiving module 103, such that the image receiving module 103 receives a first image P1 and a second image P2 generated by the device under test 102. Specifically, the image receiving module 103 forms the first image P1 and the second image P2 from the first incident light L1 and the second incident light L2 reflected by the device under test 103. The processor 104 provides a control signal S1 to the light source module 101, such that the light source module 101 adjusts the configurations of the first incident light L1 and the second incident light L2 according to the control signal S1.

It should be noted that the first incident light L1 emitted by the light source module 101 is different from the second incident light L2. The light source module 101 adjusts the configurations (such as the wavelength, the incident angle) of the incident light according to the control signal S1 generated by the processor 104, such that the configuration of the first incident light L1 is different from the configuration of the second incident light L2. In one embodiment, the incident angle of the incident light is the angle between the propagation direction of the incident light and a normal line. The normal line is perpendicular to the surface which the device under test 102 is arranged on. For example, in one embodiment, the wavelength of the first incident light L1 is different from the wavelength of the first incident light L2. In another embodiment, the incident angle of the first incident light L1 different from the incident angle 204 of the second incident light L2.

Figure 2:
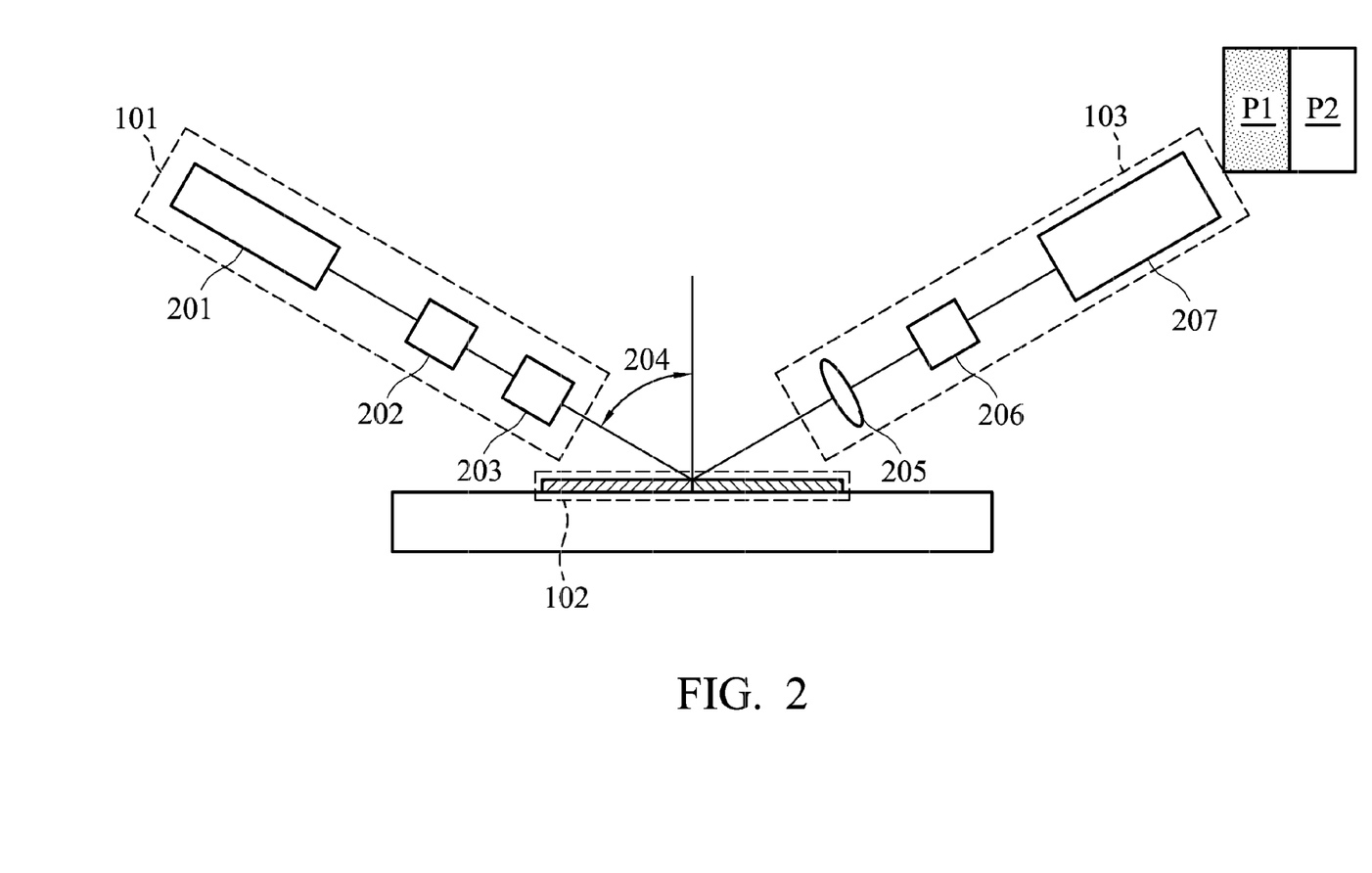
FIG. 2 is a schematic diagram of an embodiment of an inspection device according to the disclosure.

FIG. 2 is the schematic diagram of an embodiment according to the present disclosure. The light source module 101 includes a light source 201, a polarizer 202 and a compensator 203. The incident light is generated by the light source 201, and passes through the polarizer 202 and the compensator 203, and finally reaches the device under test 102. The first and the second incident lights have the same incident angle 204. The polarizer 202 polarizes the incident light to become a linear-polarized light, and the linear-polarized light passes through the compensator 203 to adjust the phase of the incident light. It should be noted that polarizer 202 and the compensator 203 can be replaced by other optical elements with similar functions, and are not limited thereto.

In addition, the image receiving module 103 includes a lens 205, an analyzer 206 and a photo-sensitive element 207. After the incident light reaches the device under test 102, it will be reflected by the device under test 102, passes the lens 205 and the analyzer 206, and finally forms an image on the photo-sensitive element 207. It should be noted that the order of the arrangement of the lens 205 and the analyzer 206 can be changed, and the lens 205, the analyzer 206 and the photo-sensitive element 207 can be replaced by other optical elements with similar functions, and are not limited thereto. In one embodiment, the photo-sensitive element 207 can be a two-dimensional photo-sensitive element. In other words, the photo-sensitive element 207 can be equipped with other devices, machines or apparatuses to sequentially obtain partial sub-images of the device under test 102 in a two-dimensional method, and then gathers all of the partial sub-images to obtain a full image of the device under test 102. In one embodiment, the photo-sensitive element 207 has a larger imaging range, such that the full image of the device under test 102 can be obtained at one time.

As shown in the embodiment of FIG. 2, the light source module 101 enables the light source 201 to sequentially emit the first incident light L1 and the second incident light L2 according to the control signal S1 from the processor 104 (not shown), wherein the wavelength of the first incident light L1 is different from the wavelength of the second incident light L2. Then the first and the second incident lights respectively pass through the polarizer 202 and the compensator 203 to the device under test 102. After that, the first incident light L1 and the second incident light L2 are sequentially reflected by the device under test 102, pass through the lens 205 and the analyzer 206, and form a first image P1 and a second image P2 on the photo-sensitive element 207. Finally, the processor 104 calculates the contrast value of the first image P1 and the second image P2 to obtain the high contrast image for inspection. The processor 104 or other electronic apparatuses determine the gray-scale value displayed by the high contrast image PF to inspect whether the device under test 102 has good uniformity or has defects. In this embodiment, the first and the second incident lights have the same incident angle 204 and the same polarization angle.

Figure 3:
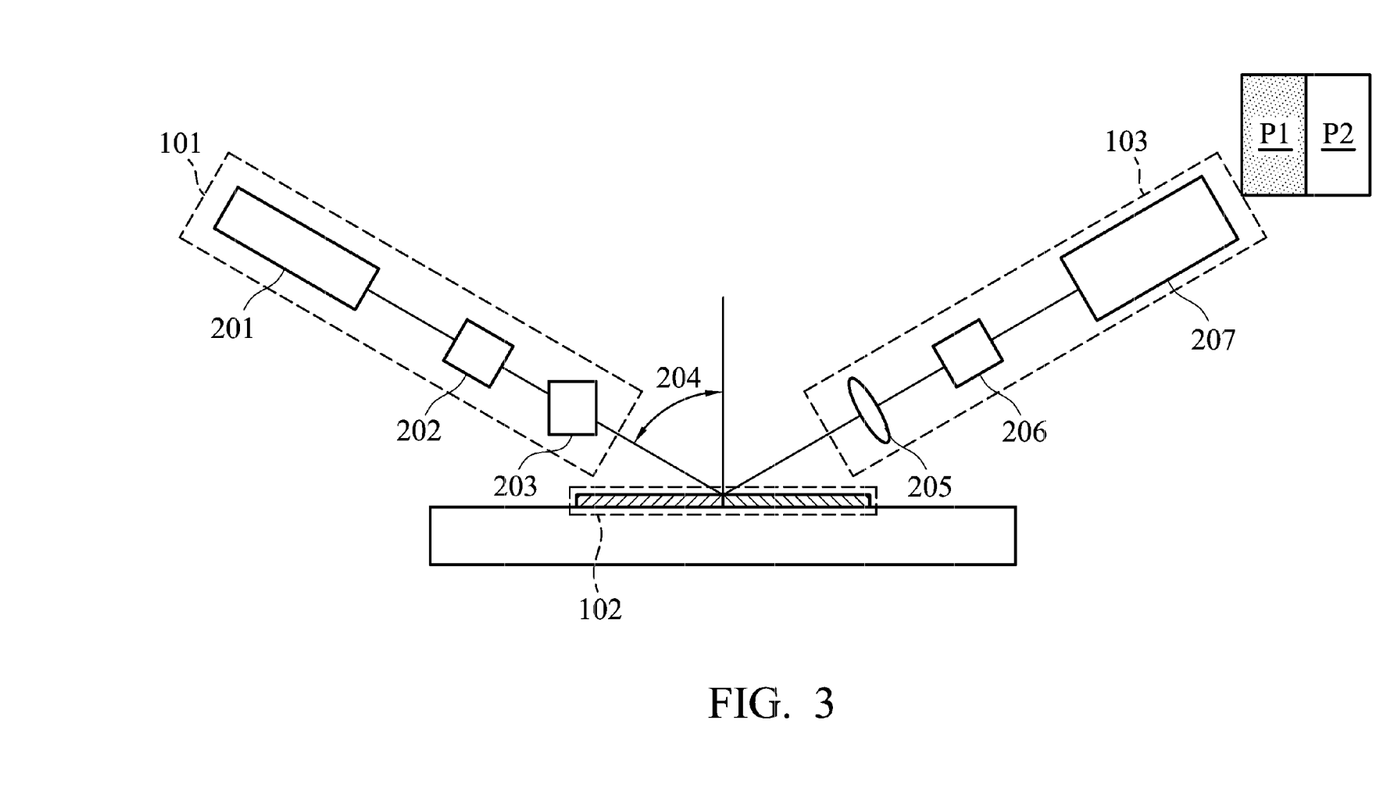
FIG. 3 is a schematic diagram of another embodiment of an inspection device according to the disclosure.

FIG. 3 is the schematic diagram of another embodiment according to the present disclosure. The light source module 101 adjusts the angles of the polarizer 202 and the phase compensator 203 respectively or at the same time according to the control signal S1 from the processor 104, such that the polarizing configuration of the first incident light L1 is different from the polarizing configuration of the second incident light L2. The light source 201 emits the first incident light L1 and the second incident light L2 sequentially. The first and the second incident lights respectively pass through the polarizer 202 and the phase compensator 203 to the device under test 102. It should be noted that the combination of the arrangements and the angles of the polarizer 202 and the phase compensator 203 passed by the first incident light L1 is different from the combination of the arrangements and the angles of the polarizer 202 and the phase compensator 203 passed by the second incident light L2. Therefore, the polarizing configurations of the first incident light L1 and the second incident light L2 are different, wherein the first incident light L1 and the second incident light L2 pass through the polarizer 202 and the phase compensator 203. Next, the first incident light L1 and the second incident light L2 are sequentially reflected by the device under test 102, pass through the lens 205 and the analyzer 206, and form a first image P1 and a second image P2 on the photo-sensitive element 207. It should be noted that in some embodiments the light source module 101 may adjust the rotation angles of the optical axises of the polarizer 202 and/or the analyzer 206, such that the polarizing configuration of the first incident light L1 is different from the polarizing configuration of the second incident light L2. In this embodiment, the first and the second incident light have the same wavelength and the incident angle 204.

Figure 4:
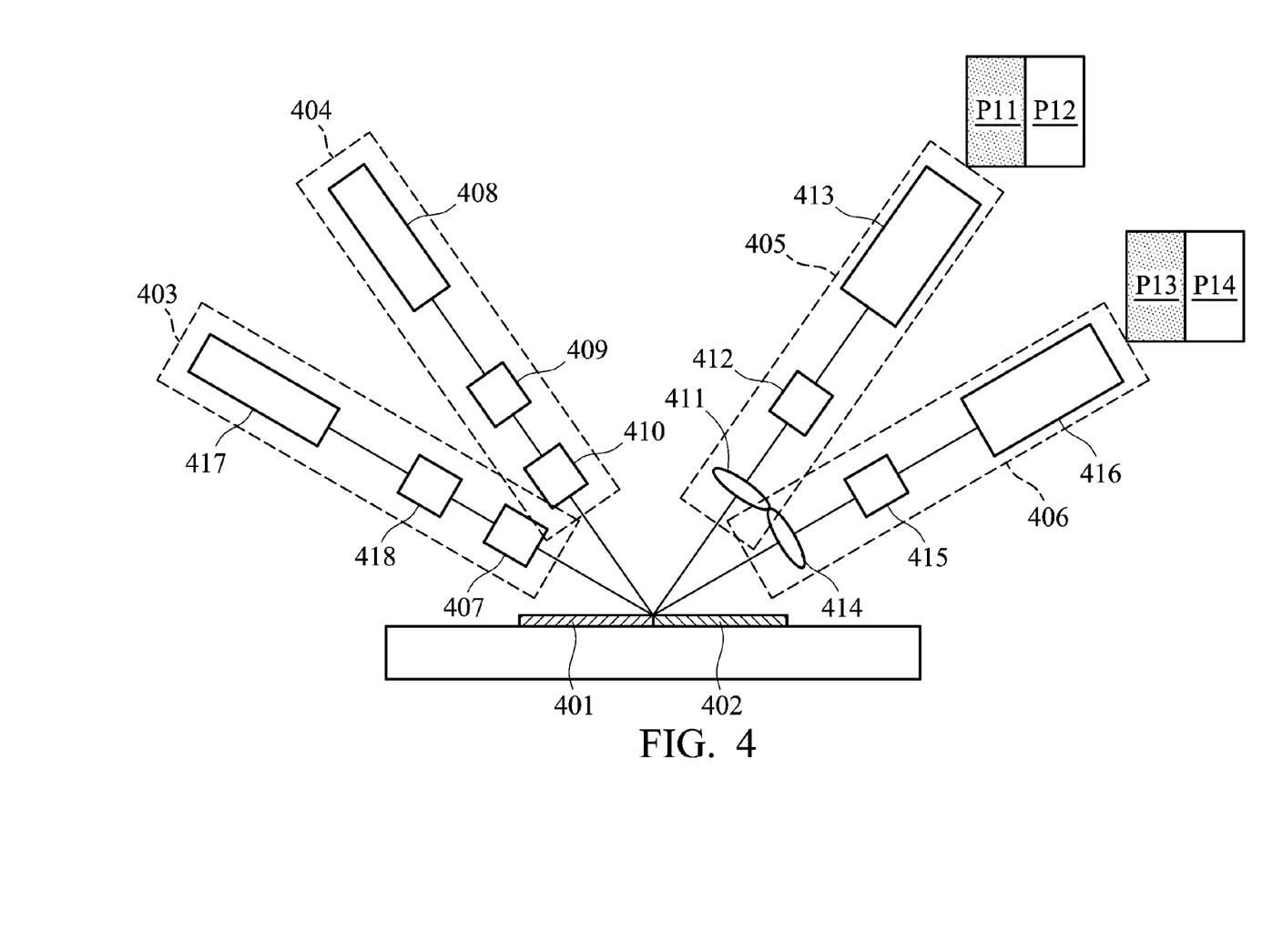
FIG. 4 is a schematic diagram of another embodiment of an inspection device according to the disclosure.

FIG. 4 is the schematic diagram of another embodiment according to the present disclosure. The light source module 101 includes a first sub-light source module 403 and a second sub-light source module 404. The first sub-light source module 403 includes a light source 417, a polarizer 418 and a compensator 407. The second sub-light source module 404 includes a light source 408, a polarizer 409 and a compensator 410. The image receiving module 105 includes a first sub-image receiving module 405 and a second sub-image receiving module 406. The first sub-image receiving module 405 includes a lens 411, an analyzer 412 and a photo-sensitive element 413. The second sub-image receiving module 406 includes lens 414, an analyzer 415 and a photo-sensitive element 416. In this embodiment, the incident angle of the first incident light L1 emitted by the first sub-light source module 403 is different from the incident angle of the second incident light L2 emitted by the second sub-light source module 404. It should be noted that, in some embodiments, the wavelength of the first incident light L1 emitted by the first sub-light source module 403 is different from the wavelength of the second incident light L2 emitted by the second sub-light source module 404. In some embodiments, the polarizing configuration of the first incident light L1 emitted by the first sub-light source module 403 is different from the polarizing configuration of the second incident light L2 emitted by the second sub-light source module 404. In other words, the combinations of the arrangement and angle of at least one of the light source 417, the polarizer 418 and the compensator 407 of the first sub-light source module 403 are different from the combinations of the arrangement and angle of at least one of the light source 408, the polarizer 409 and the compensator 410 of the second sub-light source module 404. In addition, in this embodiment, the first sub-light source module 403 and the second sub-light source module 404 generate the first incident light L1 and the second incident light L2 of any kind of incident light described above at the same time, wherein the polarizing configuration of the first incident light L1 is different from the polarizing configuration of the second incident light L2.

In the embodiment illustrated in the FIG. 4, the device under test 102 includes a first testing region 401 and a second testing region 402. The first testing region 401 and the second testing region 402 are materials of different compositions, thicknesses and/or refractive indices. For example, the first testing region 401 and the second testing region 402 can be respectively regarded as two film materials on the device under test 102 of the FIG. 1. The first sub-light source module 403 emits the first incident light L1 to the first testing region 401 and the second testing region 402 of the device under test 102. The first sub-image receiving module 405 receives a first sub-image P11 by the first incident light L1 illuminating the first testing region 401 and a second sub-image P12 by the first incident light L1 illuminating the second testing region 402. The second sub-light source module 404 emits the second incident light L2 to the first testing region 401 and the second testing region 402 of the device under test 102. The second sub-image receiving module 406 receives a third sub-image P13 by the second incident light L2 illuminating the first testing region 401 and a fourth sub-image P14 by the second incident light L2 illuminating the second testing region 402.

Then the processor 104 utilizes a predetermined formula to calculate the first sub-image P11 and the second sub-image P12 from the first sub-image receiving module 405, and the third sub-image P13 and the fourth sub-image P14 from the second sub-image receiving module 406 to generate a high contrast image PF for inspection. In one embodiment, the first sub-image P11, the second sub-image P12, the third sub-image P13, the fourth sub-image P14 and the high contrast image PF are divided into N regions. The first sub-image P11 and the second sub-image P12 can be regarded as the first image P1 of FIG. 1 to FIG. 3. The third sub-image P13 and the fourth sub-image P14 can be regarded as the second image P2 of FIG. 1 to FIG. 3. The predetermined formula is as follows:

$$PFbg(i, j) = \frac{P12bg(i, j) \times P14bg(i, j)}{|P11bg(i, j) - P13bg(i, j)|}$$

PFbg(i,j) is a gray-scale value of the high contrast image PF generated by a region (i,j) of the first testing region 401 relative to a region (i,j) of the second testing region 402. P11$bg$(i,j) is a gray-scale value of the first sub-image P11 generated by the region (i,j) of the first testing region 401. P12$bg$(i,j) is a gray-scale value of the second sub-image P12 generated by the region (i,j) of the second testing region 402. P13$bg$(i,j) is a gray-scale value of the third sub-image P13 generated by the region (i,j) of the first testing region 401. P14$bg$(i,j) is a gray-scale value of the fourth sub-image P14 generated by the region (i,j) of the second testing region 402.

Figure 5:
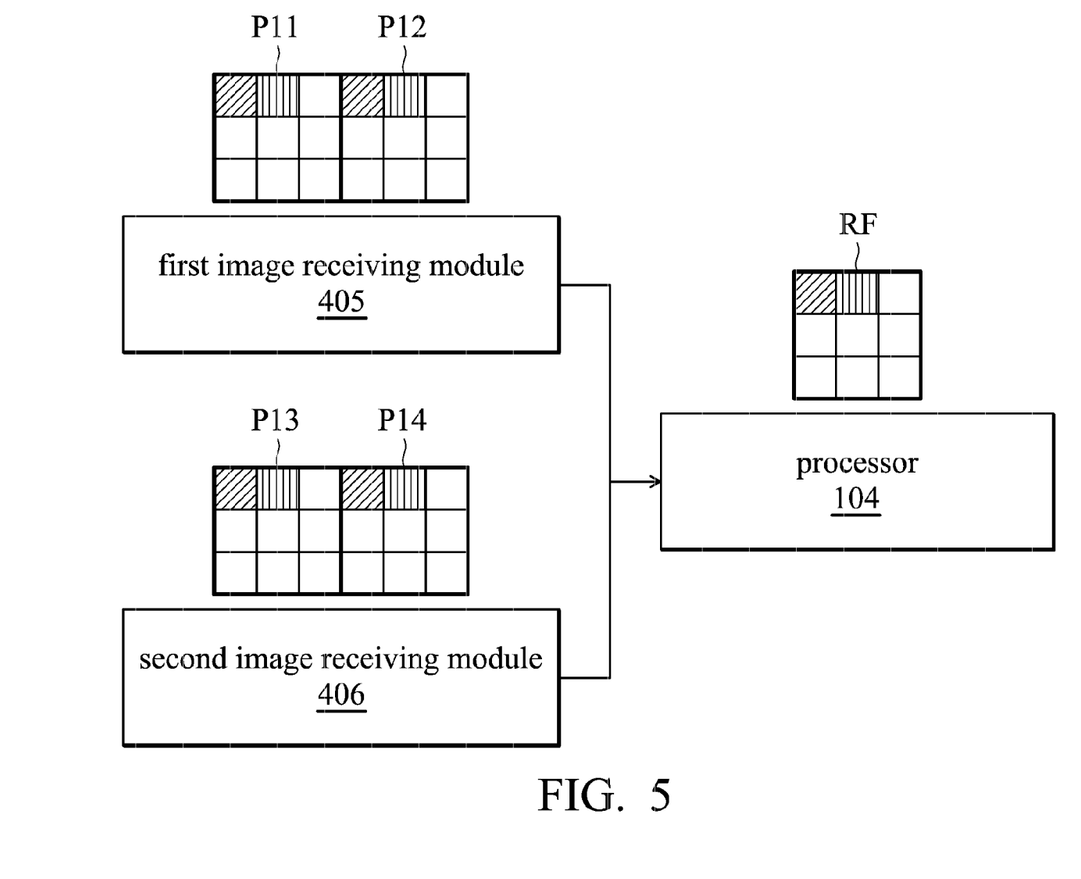
FIG. 5 is a schematic diagram of an image forming method according to the disclosure.

The first and the second sub-image receiving module 405 and 406 subsequently obtain the partial sub-images of the device under test 102 in a two-dimension method equipped with other devices, machines or apparatuses, and finally gather all of the sub-images to obtain an overall image of the device under test 102. As shown in FIG. 5, the first sub-image P1 and the second sub-image P2 received by the first sub-image receiving module 405 are the images generated by the first incident light L1 respectively illuminating the first region of the first and the second testing regions (i.e., i=1 and j=1). The third sub-image P3 and the fourth sub-image P4 received by the second sub-image receiving module 406 are the images generated by the first incident light L2 respectively illuminating the first region of the first and the second testing regions. Then the processor 104 utilizes the above predetermined formula and the gray-level values P11$bg$(1,1)~P14$bg$(1,1) of the first to the fourth sub-images to obtain a gray-level value PFbg(1,1) of the high contrast image PF, which corresponds to the first region of the first testing region relative to the first region of the second testing region. Then, the first and the second sub-image receiving modules respectively obtain the sub-images of the second region of the first and the second testing regions (i.e., i=2 and j=1). In other words, the obtained first to the fourth sub-images are the sub-images of the second regions of the first and the second testing regions. Then the processor 104 utilizes the above predetermined formula and the gray-level value P11$bg$(2,1)~P14$bg$(2,1) of the first to the fourth sub-images to obtain a gray-level value PFbg(2,1) of the high contrast image PF, which belongs to the first region of the first testing region relative to the second region of the second testing region. In conclusion, the present disclosure provides an inspection method for enhancing the contrast ratio which includes sequentially obtaining the high contrast image of the partial images of the first and the second testing regions and finally obtaining all of the high contrast images PF of the first and the second testing regions. It should be noted that, in this embodiment, the first and the second sub-image receiving modules sequentially obtain the partial images of the first and the second device under test by a two-dimensional array method. In some embodiments, the first and the second sub-image receiving modules sequentially obtain the partial or overall images of each column/row of the first and the second device under tests by a one-dimensional scan method. In some embodiments, the first and the second sub-image receiving modules obtain the overall images of the first and the second testing regions at one time. In some embodiments, the inspection device 100 includes a display panel to display the high contrast image PF generated by the processor 104.

The contrast value of the high contrast image PF calculated by the processor 104 is higher than the contrast ratio obtained by the traditional polarizing enhancement contrast method. Thus, a high contrast image PF with a clearer gray-scale display can be obtained. The processor 104, the operator of the device or other electronic apparatuses determine the gray-scale value displayed by the high contrast image PF, so whether the device under test 102 has good uniformity or defects can be inspected. In some embodiments, when the gray-scale value of a certain region of the high contrast image PF is higher or lower than the gray-scale value of other regions, it indicates that the certain region with defects has been inspected or the physical parameters (such as thickness, refractive index an so on) of the certain region is different from that of other regions. In one embodiment, the first testing region 401 of the device under test 102 becomes the second testing region 402 by the treatment of a certain manufacturing process. The inspection device according to the present disclosure determines the high contrast image PF of the device under test 102 to inspect the physical characteristics, uniformity and defects of the second testing region 402 treated by a certain manufacturing process.

Figure 6:
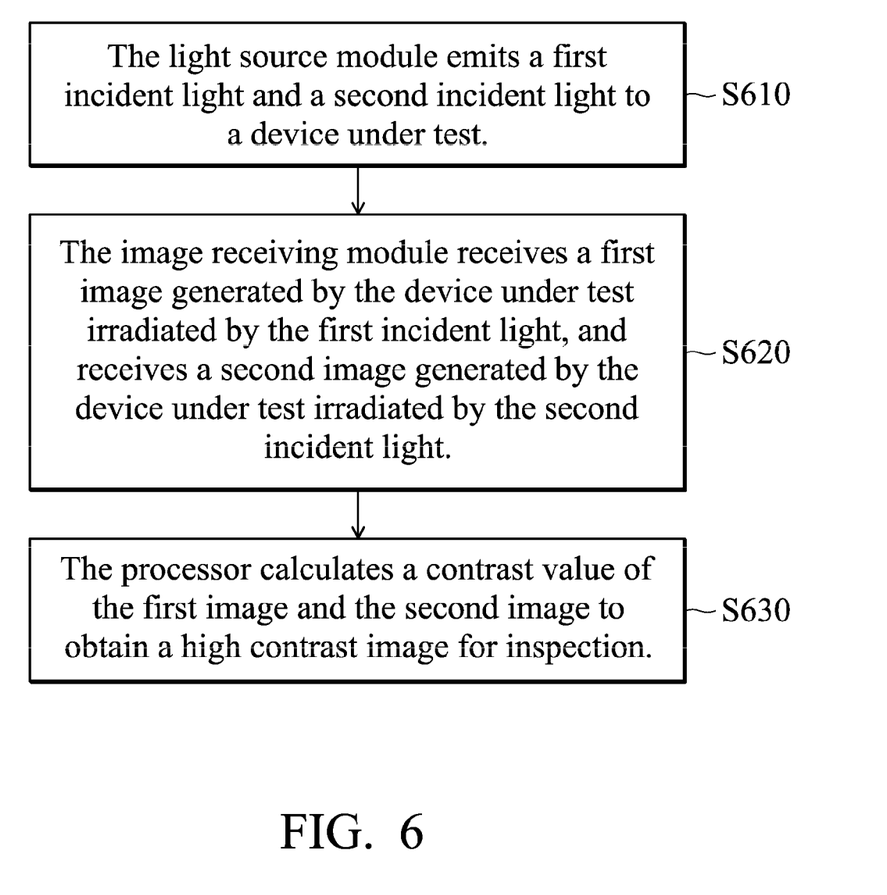
FIG. 6 is an operation flowchart of the inspection device according to the disclosure.

FIG. 6 is a flowchart of an inspection device according to the present disclosure. At first, in the step S610, the light source module 101 emits a first incident light L1 and a second incident light L2 to a device under test 102. The light source module 101 emits the first and second incident lights sequentially or at the same time. In addition, the wavelength, the incident angle and/or the polarizing configuration of the first incident light L1 and the second incident light L2 are different, and the device under test 102 includes more than two materials of different compositions, thicknesses and/or refractive indices. In the step S620, the image receiving module 103 receives a first image P1 generated by the device under test 102 irradiated by the first incident light L1, and receives a second image P2 generated by the device under test 102 irradiated by the second incident light L2. Finally, in step S630, the processor 104 calculates a contrast value of the first image P1 and the second image P2 to obtain a high contrast image PF for inspection. The processor 104 or other electronic devices determine the gray-scale value of the high contrast image PF to inspect the physical characteristics, uniformity and defects of the device under test 102.

While the disclosure has been described by way of example and in terms of the preferred embodiments, it is to be understood that the disclosure is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An inspection device, comprising: a light source module, emitting a first incident light and a second incident light to a device under test (DUT); an image receiving module, receiving a first image generated by the DUT irradiated by the first incident light and a second image generated by the DUT irradiated by the second incident light; and a processor, calculating a contrast value of the first image and the second image to obtain a high contrast image for inspection; wherein the DUT comprises a first testing region and a second testing region, and the image receiving module receives a first sub-image generated by the first incident light illuminating the first testing region, a second sub-image generated by the first incident light illuminating the second testing region, a third sub-image generated by the second incident light illuminating the first testing region, and a fourth sub-image generated by the second incident light illuminating the second testing region, and the processor utilizes a predetermined formula to calculate contrast values of the first sub-image, the second sub-image, the third sub-image and the fourth sub-image to obtain the high contrast image for inspection, wherein each of the first sub-image, the second sub-image, the third sub-image, the fourth sub-image and the high contrast image is divided into N regions by the following formula:

$$PFbg(i, j) = \frac{P12bg(i, j) \times P14bg(i, j)}{|P11bg(i, j) - P13bg(i, j)|}$$

wherein $PFbg(i,j)$ is a gray-scale value of the high contrast image PF generated by a region (i,j) of the first testing region relative to a region (i,j) of the second testing region, and $P11bg(i,j)$ is a gray-scale value of the first sub-image generated by the region (i,j) of the first testing region, and $P12bg(i,j)$ is a gray-scale value of the second sub-image generated by the region (i,j) of the second testing region, and $P13bg(i,j)$ is a gray-scale value of the third sub-image generated by the region (i,j) of the first testing region, and $P14bg(i,j)$ is a gray-scale value of the fourth sub-image generated by the region (i,j) of the second testing region.

2. The inspection device as claimed in claim 1, wherein a wavelength of the first incident light is different from a wavelength of the second incident light.

3. The inspection device as claimed in claim 1, wherein an incident angle of the first incident light is different from an incident angle of the second incident light.

4. The inspection device as claimed in claim 1, wherein the light source module comprises a polarizer and a compensator, and the image receiving module comprises an analyzer and a photo-sensitive element, such that the first incident light and the second incident light pass through the polarizer and the compensator to the DUT, and the photo-sensitive element obtains the first image and the second image by the analyzer.

5. The inspection device as claimed in claim 4, wherein the optical axises of the polarizer, the compensator and/or the analyzer are different such that a polarizing configuration of the first incident light is different from a polarizing configuration of the second incident light.

6. The inspection device as claimed in claim 1, wherein the processor determines whether the DUT has defects by a gray-scale value of the high contrast image.

7. The inspection device as claimed in claim 1, wherein the light source module includes a first sub-light source module and a second sub-light source module emitting the first incident light and the second incident light to the DUT respectively, and the image receiving module further includes a first sub-image receiving module and a second sub-image receiving module respectively receiving a first image generated by the DUT irradiated by the first incident light and a second image generated by the DUT irradiated by the second incident light.

8. The inspection device as claimed in claim 7, wherein the first sub-image receiving module and the second sub-image receiving module respectively emit the first incident light and the second incident light to the DUT at the same time.

9. The inspection device as claimed in claim 7, wherein the first sub-light source module and the second sub-light source module respectively comprise a polarizer and a compensator, the first sub-image receiving module and the second sub-image receiving module further respectively comprise an analyzer and a photo-sensitive element, such that the first incident light and the second incident light pass through the polarizers and the compensators of the first sub-light source module and the second sub-light source module respectively to the DUT, and the photo-sensitive element obtains the first image and the second image by the analyzers of the first sub-image receiving module and the second sub-image receiving module respectively, wherein the optical axises of the polarizers, the compensators and/or the analyzers are different such that the polarizing configuration of the first incident light is different from the polarizing configuration of the second incident light.

10. An inspection method, applied to an inspection device, wherein the inspection device comprises a light source module, an image receiving module and a processor, the inspection method comprising: emitting a first incident light and a second incident light to a device under test (DUT) by the light source module; receiving a first image generated by the DUT irradiated by the first incident light and a second image generated by the DUT irradiated by the second incident light; and calculating a contrast value of the first image and the second image to obtain a high contrast image for inspection by the processor; wherein the DUT further comprises a first testing region and a second testing region, and the image receiving module receives a first sub-image generated by the first incident light illuminating the first testing region, a second sub-image generated by the first incident light illuminating the second testing region, a third sub-image generated by the second incident light illuminating the first testing region, and a fourth sub-image generated by the second incident light illuminating the second testing region, and the processor utilizes a predetermined formula to calculate the contrast values of the first sub-image, the second sub-image, the third sub-image and the fourth sub-image to obtain the high contrast image for inspection, wherein each of the first sub-image, the second sub-image, the third sub-image, the fourth sub-image and the high contrast image is divided into N regions by the following formula:

$$PFbg(i, j) = \frac{P12bg(i, j) \times P14bg(i, j)}{|P11bg(i, j) - P13bg(i, j)|}$$

wherein PFbg(i,j) is a gray-scale value of the high contrast image PF generated by a region (i,j) of the first testing region relative to a region (i,j) of the second testing region, and P11bg(i,j) is a gray-scale value of the first sub-image generated by the region (i,j) of the first testing region, and P12bg(i,j) is a gray-scale value of the second sub-image generated by the region (i,j) of the second testing region, and P13bg(i,j) is a gray-scale value of the third sub-image generated by the region (i,j) of the first testing region, and P14bg(i,j) is a gray-scale value of the fourth sub-image generated by the region (i,j) of the second testing region.

11. The inspection method as claimed in claim 10, wherein a wavelength of the first incident light is different from a wavelength of the second incident light.

12. The inspection method as claimed in claim 10, wherein an incident angle of the first incident light is different from an incident angle of the second incident light.

13. The inspection method as claimed in claim 10, wherein the first incident light and the second incident light pass through a polarizer and a compensator of the light source module to the DUT, and the first image and the second image are obtained by a photo-sensitive element of the image receiving module through an analyzer.

14. The inspection method as claimed in claim 13, wherein the optical axises of the polarizer, the compensator and/or the analyzer are different such that a polarizing configuration of the first incident light is different from a polarizing configuration of the second incident light.

15. The inspection method as claimed in claim 10, further comprising determining whether the DUT has defects by a gray-scale value of the high contrast image.

16. The inspection method as claimed in claim 10, wherein the light source module includes a first sub-light source module and a second sub-light source module emitting the first incident light and the second incident light to the DUT respectively, and the image receiving module includes a first sub-image receiving module and a second sub-image receiving module respectively receiving a first image generated by the DUT irradiated by the first incident light and a second image generated by the DUT irradiated by the second incident light.

17. The inspection method as claimed in claim 16, wherein the first sub-image receiving module and the second sub-image receiving module emit the first incident light and the second incident light to the DUT at the same time.

18. The inspection method as claimed in claim 16, wherein the first sub-light source module and the second sub-light source module respectively comprise a polarizer and a compensator, the first sub-image receiving module and the second sub-image receiving module further respectively comprise an analyzer and a photo-sensitive element, such that the first incident light and the second incident light pass through the polarizers and the compensators of the first sub-light source module and the second sub-light source module respectively to the DUT, and the photo-sensitive element obtains the first image and the second image by the analyzers of the first sub-image receiving module and the second sub-image receiving module respectively, wherein the optical axises of the polarizers, the compensators and/or the analyzers are different such that the polarizing configuration of the first incident light is different from the polarizing configuration of the second incident light.

* * * * *